US011925396B2

(12) United States Patent
Biedermann

(10) Patent No.: US 11,925,396 B2
(45) Date of Patent: Mar. 12, 2024

(54) LOCKING ELEMENT FOR A POLYAXIAL BONE ANCHOR, BONE PLATE ASSEMBLY AND TOOL

(71) Applicant: Biedermann Technologies Gmbh & Co. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 18/076,811

(22) Filed: Dec. 7, 2022

(65) Prior Publication Data

US 2023/0145753 A1  May 11, 2023

Related U.S. Application Data

(63) Continuation of application No. 16/683,215, filed on Nov. 13, 2019, now Pat. No. 11,547,458, which is a (Continued)

(30) Foreign Application Priority Data

Mar. 29, 2010 (EP) .................................. 10158246

(51) Int. Cl.
*A61B 17/80* (2006.01)
*A61B 17/86* (2006.01)
(Continued)

(52) U.S. Cl.
CPC ...... *A61B 17/8057* (2013.01); *A61B 17/8042* (2013.01); *A61B 17/808* (2013.01);
(Continued)

(58) Field of Classification Search
CPC ............ A61B 17/8042; A61B 17/8033; A61B 17/808; A61B 17/8605; A61B 17/861;
(Continued)

(56) References Cited

U.S. PATENT DOCUMENTS 2,813,450 A * 11/1957 Dzus ....................... F16D 1/101
81/436
4,480,513 A    11/1984 McCauley
(Continued)

FOREIGN PATENT DOCUMENTS

CN        1092637      9/1994
EP        0938872      9/1999
(Continued)

OTHER PUBLICATIONS

Chinese OA for Application No. 201180013246.7, dated Aug. 11, 2014 (11 sheets), and English translation (10 sheets).
(Continued)

*Primary Examiner* — Marcela I. Shirsat
(74) *Attorney, Agent, or Firm* — Gordon & Jacobson, P.C.

(57) ABSTRACT

A tool adapted for use with a bone plate assembly includes a driver with an engagement portion configured to engage a locking element, and a tubular holder. The driver may be configured to extend with the engagement portion through the tubular holder, and may be axially movable and rotatable within the holder. The holder may have a radial slot adapted for insertion of the locking element. The holder may include a portion with an internal thread for cooperation with an external thread of the locking element. The locking element may be used with a polyaxial bone anchor.

13 Claims, 11 Drawing Sheets

Related U.S. Application Data continuation of application No. 14/323,717, filed on Jul. 3, 2014, now Pat. No. 10,499,964, which is a continuation of application No. 13/039,422, filed on Mar. 3, 2011, now Pat. No. 8,808,335.

(60) Provisional application No. 61/369,495, filed on Jul. 30, 2010, provisional application No. 61/311,517, filed on Mar. 8, 2010.

(51) Int. Cl.
  *A61B 17/88* (2006.01)
  *F16B 23/00* (2006.01)

(52) U.S. Cl.
  CPC ........ *A61B 17/8605* (2013.01); *A61B 17/861* (2013.01); *A61B 17/8615* (2013.01); *A61B 17/8875* (2013.01); *A61B 17/8877* (2013.01); *A61B 17/8033* (2013.01); *F16B 23/0007* (2013.01); *F16B 23/003* (2013.01); *F16B 23/0061* (2013.01)

(58) Field of Classification Search
  CPC ............. A61B 17/8875; A61B 17/8877; F16B 23/0007; F16B 23/003; F16B 23/0061
  USPC ........................................................ 606/291
  See application file for complete search history.

(56) References Cited

U.S. PATENT DOCUMENTS

| | | |
|---|---|---|
| 5,180,381 A | 1/1993 | Aust |
| 5,370,486 A | 12/1994 | Plummer |
| 5,520,690 A | 5/1996 | Errico |
| 5,531,746 A | 7/1996 | Errico |
| 5,534,027 A | 7/1996 | Hodorek |
| 5,607,426 A | 3/1997 | Ralph |
| 5,674,222 A | 10/1997 | Berger |
| 5,814,046 A | 9/1998 | Hopf |
| 5,879,389 A | 3/1999 | Koshino |
| 5,885,286 A | 3/1999 | Sherman |
| 5,904,683 A * | 5/1999 | Pohndorf ............ A61B 17/8042 606/295 |
| 6,022,350 A | 2/2000 | Ganem |
| 6,102,951 A | 8/2000 | Sutter |
| 6,102,952 A | 8/2000 | Koshino |
| 6,139,550 A | 10/2000 | Michelson |
| 6,146,383 A | 11/2000 | Studer |
| 6,290,703 B1 | 9/2001 | Ganem |
| 6,383,186 B1 | 5/2002 | Michelson |
| 6,423,068 B1 | 7/2002 | Reisberg |
| 6,440,135 B2 | 8/2002 | Orbay |
| 6,585,738 B1 | 7/2003 | Mangione |
| 6,595,993 B2 | 7/2003 | Donno |
| 6,767,351 B2 | 7/2004 | Orbay |
| 6,893,444 B2 | 5/2005 | Orbay |
| 7,077,844 B2 | 7/2006 | Michelson |
| 7,097,645 B2 | 8/2006 | Michelson |
| 7,112,202 B2 | 9/2006 | Michelson |
| 7,118,573 B2 | 10/2006 | Michelson |
| 7,186,256 B2 | 3/2007 | Michelson |
| 7,399,301 B2 | 7/2008 | Michelson |
| 7,476,228 B2 | 1/2009 | Abdou |
| 7,527,639 B2 | 5/2009 | Orbay |
| 7,547,306 B2 | 6/2009 | Michelson |
| 7,563,263 B2 | 7/2009 | Orbay |
| 7,651,497 B2 | 1/2010 | Michelson |
| 7,780,711 B2 | 8/2010 | Orbay |
| 7,811,285 B2 | 10/2010 | Michelson |
| 7,985,224 B2 | 7/2011 | Michelson |
| 8,048,075 B2 | 11/2011 | Michelson |
| 8,123,788 B2 | 2/2012 | Michelson |
| 8,262,708 B2 | 9/2012 | Michelson |
| 8,480,717 B2 | 7/2013 | Michelson |
| 8,556,985 B2 | 10/2013 | Meridew |
| 8,574,272 B2 | 11/2013 | Wallenstein |
| 8,808,335 B2 | 8/2014 | Biedermann |
| 10,499,964 B2 | 12/2019 | Biedermann |
| 11,547,458 B2 | 1/2023 | Biedermann |
| 2001/0021851 A1 | 9/2001 | Eberlein |
| 2001/0047174 A1 | 11/2001 | Donno |
| 2004/0153073 A1 | 8/2004 | Orbay |
| 2004/0172028 A1 | 9/2004 | Roger |
| 2004/0181226 A1 | 9/2004 | Michelson |
| 2004/0260293 A1 | 12/2004 | Orbay |
| 2004/0260295 A1 | 12/2004 | Orbay |
| 2005/0010219 A1 | 1/2005 | Dalton |
| 2005/0240186 A1 | 10/2005 | Orbay |
| 2005/0273131 A1 * | 12/2005 | Shluzas ............ A61B 17/7007 606/198 |
| 2006/0041260 A1 | 2/2006 | Orbay |
| 2006/0264962 A1 | 11/2006 | Chin |
| 2006/0276793 A1 | 12/2006 | Berry |
| 2008/0200955 A1 | 8/2008 | Tepic |
| 2009/0036932 A1 | 2/2009 | Rouyer |
| 2009/0062866 A1 | 3/2009 | Jackson |
| 2009/0163962 A1 | 6/2009 | Dauster |
| 2009/0210067 A1 | 8/2009 | Meridew |
| 2010/0211112 A1 | 8/2010 | Kuster |
| 2010/0256688 A1 * | 10/2010 | Giersch ................ A61B 17/864 606/301 |
| 2011/0137314 A1 | 6/2011 | Kuster |
| 2013/0296942 A1 | 11/2013 | Michelson |
| 2014/0358186 A1 * | 12/2014 | Frock ................. A61B 17/8891 606/86 A |

FOREIGN PATENT DOCUMENTS

| | | |
|---|---|---|
| EP | 0988833 | 3/2000 |
| EP | 1935356 | 6/2008 |
| FR | 2697991 | 5/1994 |
| JP | 2002291762 | 10/2002 |
| WO | 9410928 | 5/1994 |
| WO | 9905968 | 2/1999 |
| WO | 0004836 | 2/2000 |
| WO | 0215806 | 2/2002 |
| WO | 03101321 | 12/2003 |
| WO | 2005058134 | 6/2005 |
| WO | 2009043827 | 4/2009 |

OTHER PUBLICATIONS

Partial Eropean Search Report of Application No. EP17153 947.1 dated Aug. 17, 2016 (13 pages).
U.S. Appl. No. 61/311,517, filed Mar. 8, 2010.
U.S. Appl. No. 61/369,495, filed Jul. 30, 2010.

* cited by examiner

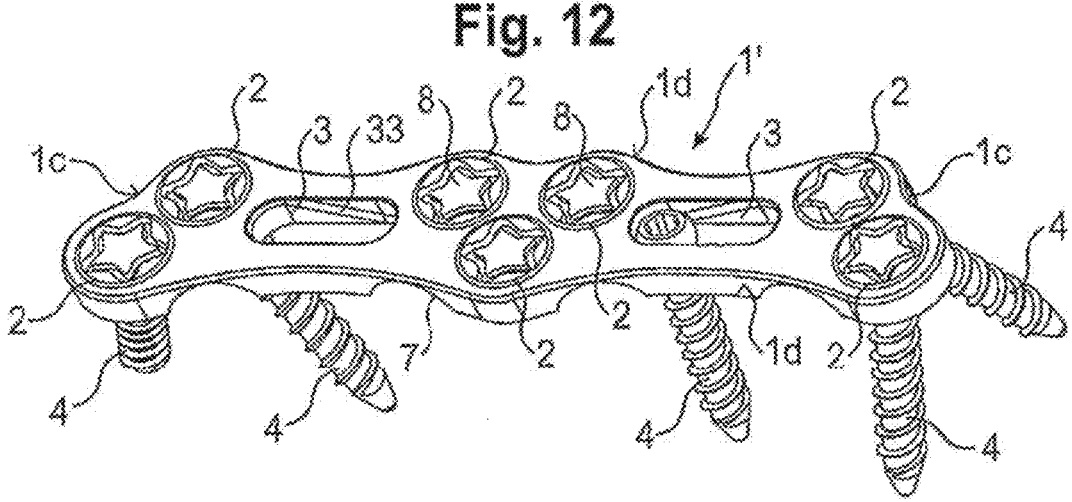
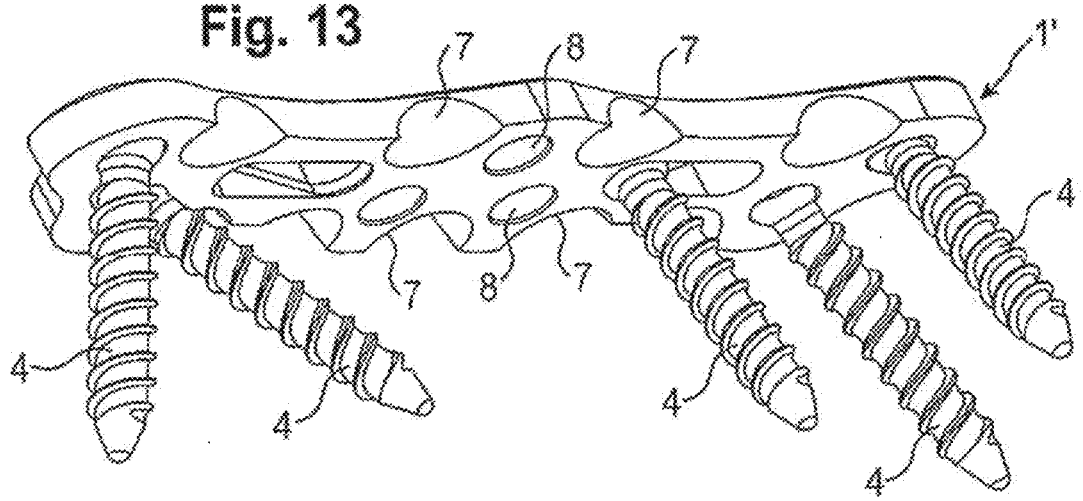
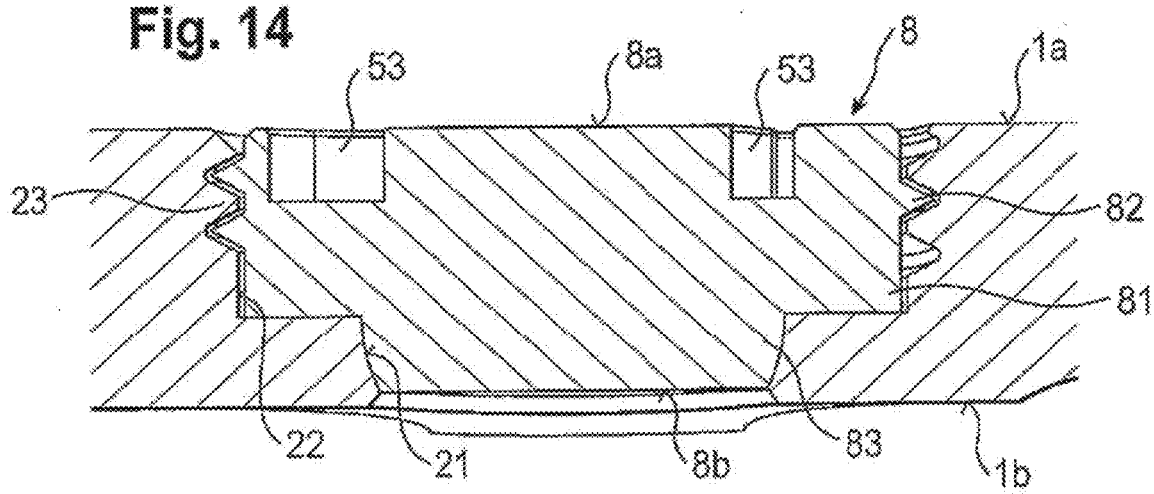

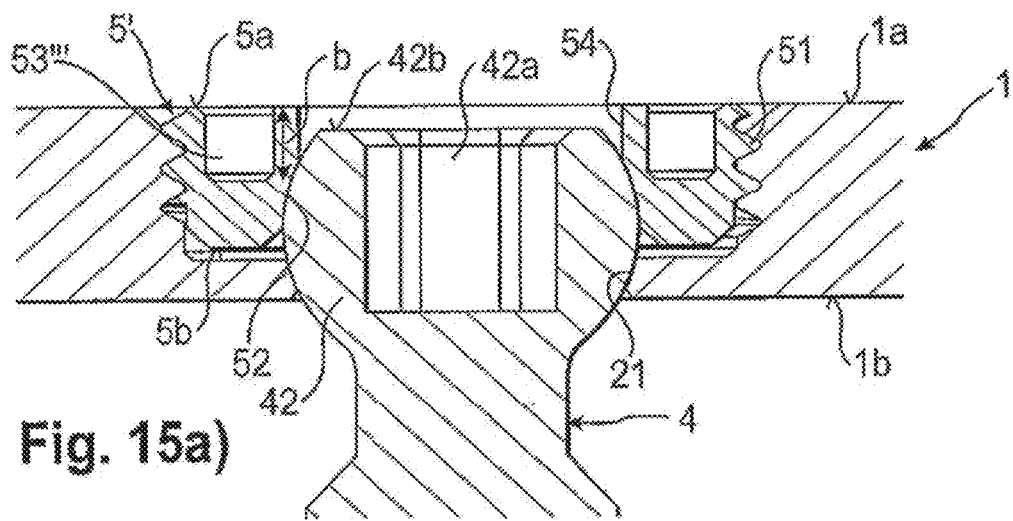
Fig. 15a)
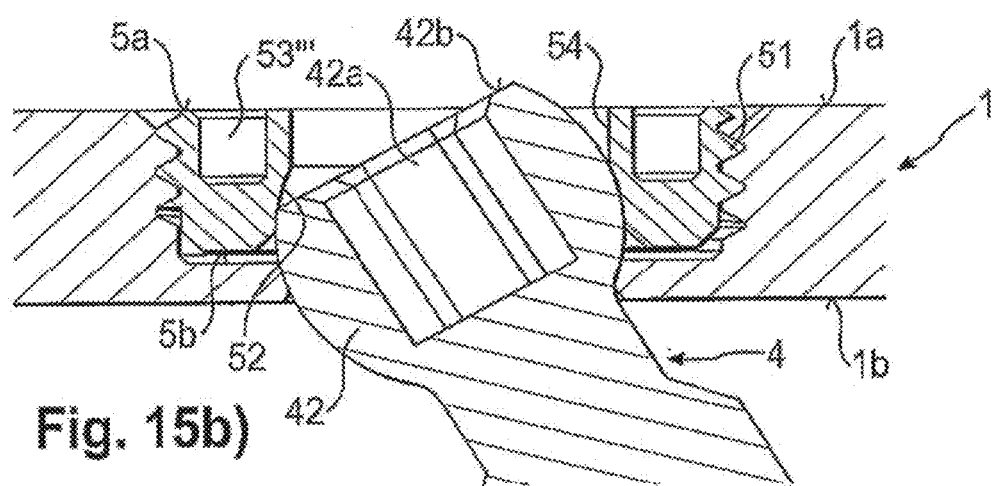
Fig. 15b)
Fig. 16
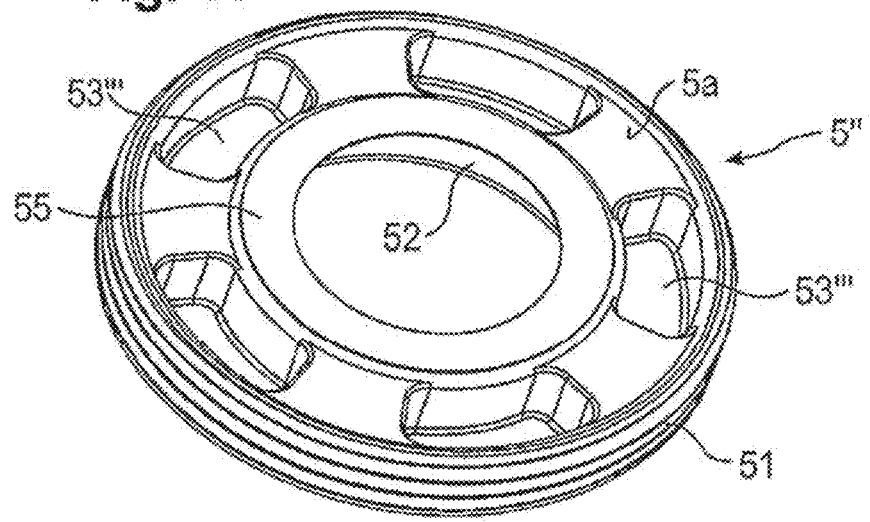

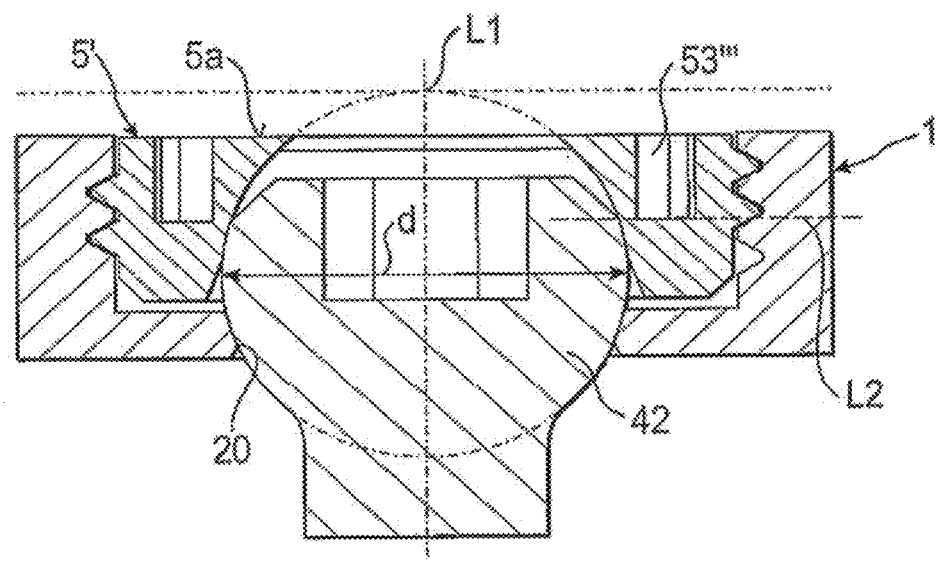
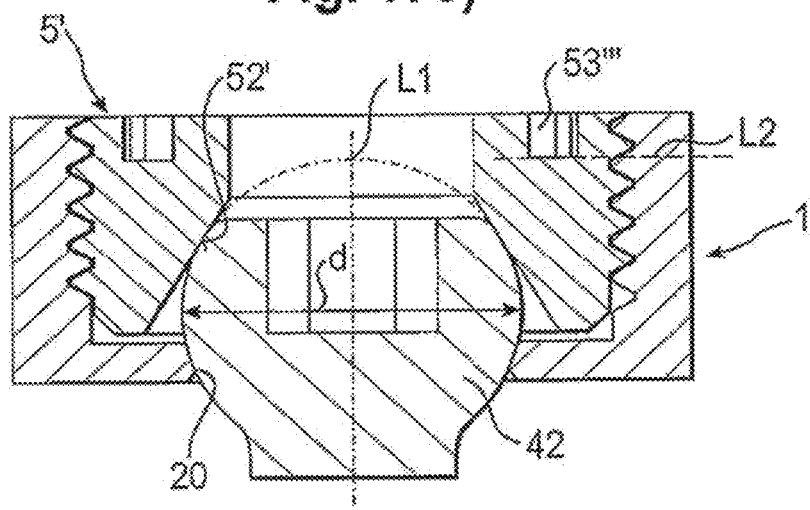

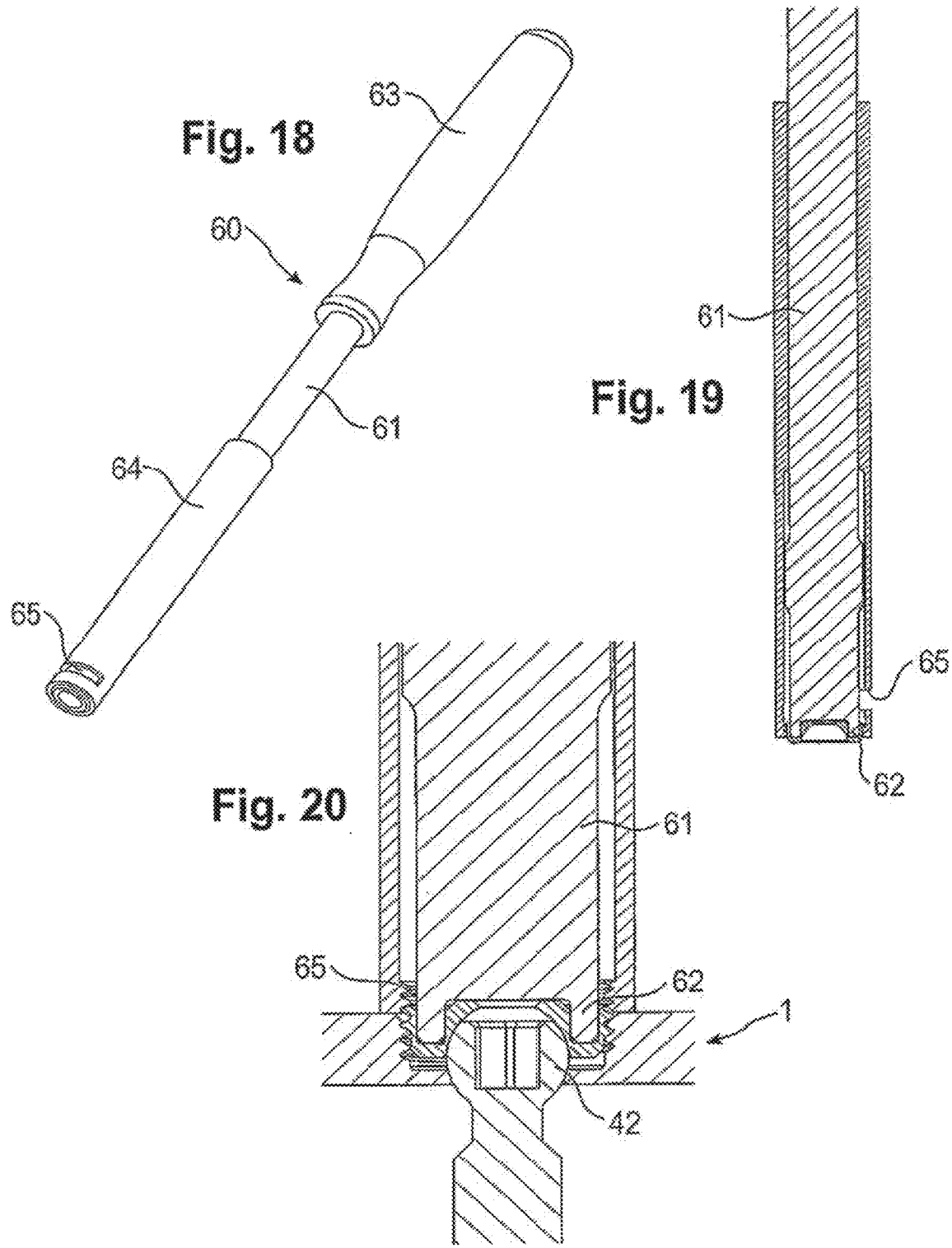

LOCKING ELEMENT FOR A POLYAXIAL BONE ANCHOR, BONE PLATE ASSEMBLY AND TOOL

CROSS-REFERENCE TO RELATED APPLICATIONS

This application is a continuation of U.S. Ser. No. 16/683,215, filed Nov. 13, 2019, which is a continuation of U.S. Ser. No. 14/323,717, filed Jul. 3, 2014, now issued as U.S. Pat. No. 10,499,964, which is a continuation of U.S. Ser. No. 13/039,422, filed Mar. 3, 2011, now issued as U.S. Pat. No. 8,808,335, which claims priority to and wholly incorporates by reference US provisional patent application No. 61/311,517 filed Mar. 8, 2010, U.S. provisional patent application No. 61/369,495 filed Jul. 30, 2010, and European patent application no. EP10158246.8 filed Mar. 29, 2010, all of which are hereby incorporated by reference herein in their entireties.

BACKGROUND

1. Field of the Invention

The invention relates to a locking element for a polyaxial bone anchor and to a bone plate assembly for the immobilization of bones or bone fragments or vertebrae and a tool used therefor. Particularly, the invention relates to a bone plate assembly with a polyaxial coupling between the bone anchors of the bone plate assembly and a plate with an increased range of angular motion and low profile.

2. State of the Art

U.S. Pat. No. 6,022,350 describes a bone fixing device comprising an elongate single-piece plate-shaped element receiving at least one bone-fastening screw which passes through an orifice formed in the plate-shaped element. The head of the screw includes an essentially spherical surface for bearing against a bearing surface of essentially circular cross-section in the bottom of the plate element. The device further includes a plug for coming into clamping contact against said screw head to hold it in a desired angular position. The outside face of the plug includes a central tightening socket which is identical to that in the screw head so that the same tightening tool can be used.

U.S. Pat. No. 5,531,746 describes a polyaxial screw plate assembly for immobilization of vertebral bones including an elongate plate having a plurality of holes wherein the bottom portion of the holes has a curved interior surface which forms an annular lip for supporting a semi-spherical head portion of a bone screw. A coupling element in the form of a short threaded cylindrical piece having a concave bottom locks the screw into the hole.

In addition, various bone plate assemblies are known which use bushings with a spherical exterior surface which can pivot in holes with a spherical interior surface and which encompass a screw head to provide polyaxial angular adjustability of bone screws relative to the plate. Examples of such assemblies are known, for example, from WO 99/05968 and WO 00/04836.

SUMMARY

While the known bone plate assemblies can provide polyaxial adjustment of the bone anchors relative to the plate, there is still a need for an improved bone plate assembly which allows for a greater range of angular positions, a lower profile of the plate-screw construct and a variety of usage.

It is therefore the object of the invention to provide a low profile bone plate assembly and a locking element for a polyaxial bone anchor and a tool therefor which allows a polyaxial adjustment of the bone anchor and the plate with a wide range of angular motion with a simple design while simultaneously providing a high safety of use.

The object is solved by a locking element and a bone plate assembly according to the claims of the present invention.

The bone plate assembly according to the invention allows a pivot angle of the bone anchor relative to the plate of up to around 35° with respect to the vertical position. This corresponds to a motion cone of up at least 60°. The position of the bone anchor relative to the plate has an angular stability due to the locking element. The locking can be carried out by application of low torque. With the locking element, the screws are secured against pull-out. Different locking elements can be provided to achieve either full locking or frictional locking or to allow free angulation while only preventing pull-out of the anchor.

In addition, the bone plate assembly is designed with a minimum of necessary parts and has a low profile. Due to the simple design and the small number of parts which are setting up the bone plate assembly, it is economical to manufacture.

The holes for the bone anchors in the plate member are designed such that bone anchors with or without a locking member can be used. Additionally, locking plugs can be provided to close a hole without the use of a bone anchor, for example, if there are small bone fragments or for ensuring stability against cracking.

Furthermore, the plate member may have offset holes which are offset from a central longitudinal line for more variety of usage. The plate member can be designed to have a minimal bone contact area and can be used as a dynamic plate. Also, the plate member may be contoured to provide a specific shape for specific clinical applications.

The bone plate assembly is suitable for various clinical applications. For example, due to the low profile design, the bone plate assembly is suitable for the application in areas with minimal soft tissue coverage like the cervical spine or other small bones like the clavicle or the pelvis.

Further features and advantages of the invention will become apparent from the description of embodiments with reference to the accompanying drawings.

DESCRIPTION OF THE DRAWINGS

FIG. 12 shows a perspective view from the top of a second embodiment of the bone plate assembly.

FIG. 13 shows a perspective view from the bottom of the bone plate assembly of FIG. 12.

FIG. 14 shows an enlarged schematic sectional view of a hole of the bone plate according to FIG. 12 sealed by a plug member.

FIG. 15a) shows a schematic sectional view of a further embodiment of the bone plate assembly including the hole, the bone screw and a modified locking element, wherein the bone screw is in a straight position.

FIG. 15b) shows the bone plate assembly of FIG. 15a) with the bone screw in an angled position.

FIG. 16 shows an enlarged perspective view of the locking element of the embodiment according to FIGS. 15a) and 15b).

FIG. 18 shows a perspective view of a tool for inserting the locking element.

FIG. 19 shows an enlarged schematic sectional view of a portion of the tool of FIG. 18.

FIG. 20 shows a further enlarged schematic sectional view of a portion of the bone plate with a polyaxial bone screw, the locking element and the tool.

DESCRIPTION OF EMBODIMENTS

Figure 1:
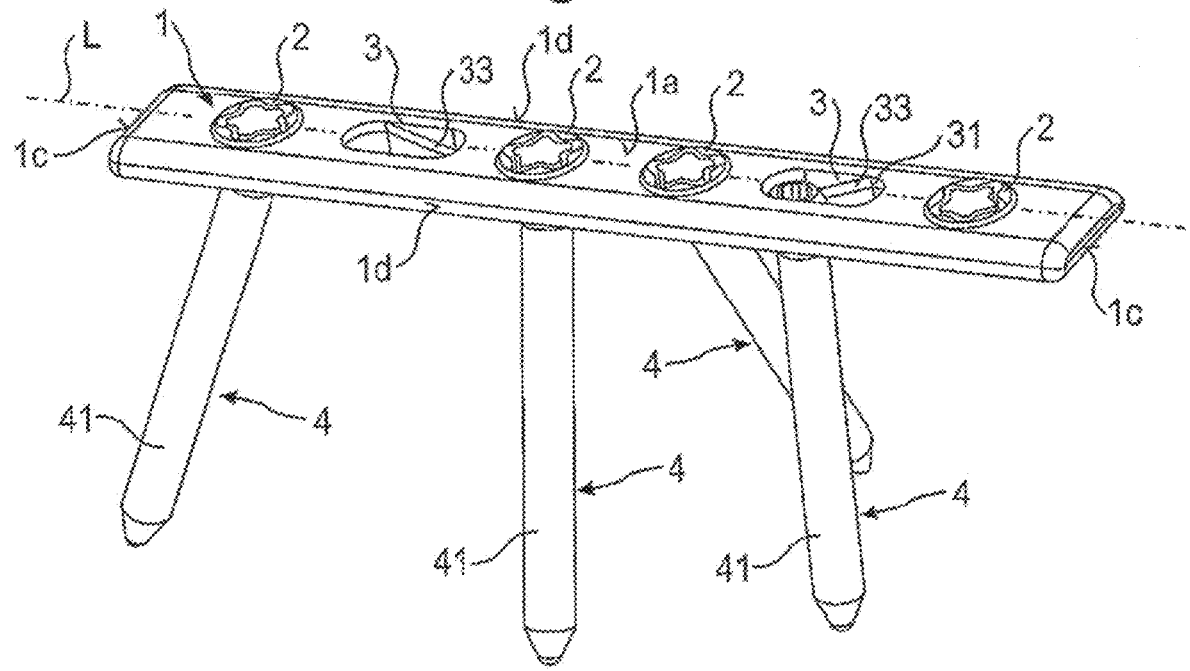
FIG. 1 shows a perspective view of a bone plate assembly according to a first embodiment.

A first embodiment of the bone plate assembly will now be described with reference to FIGS. 1 to 9. As can be seen in particular in FIGS. 1 and 2 the bone plate assembly includes a plate member 1 which is in this embodiment a substantially rectangular body with a top side 1a, a bottom side $1_b$, short sides $1_c$ and long sides $1_d$ and a longitudinal axis L. A plurality of first holes 2 extend through the plate member from the top side 1a to the bottom side 1b. Second holes 3 can be provided which are, for example, arranged between the first holes 2 also extend from the top side 1a to the bottom side 1b. However, the number and arrangement of first and second holes can vary according to the size and shape of the plate member 1. The plate member may have only first holes 2 and the second holes 3 can be omitted.

The bone plate assembly further comprises a plurality of bone anchors in form of bones screws 4 which can be inserted into the first holes 2 and/or the second holes 3. The bone screw 4 has a threaded shank 41 with a tip and a head 42. The head 42 has a spherical exterior surface portion and a recess 42a at its free end 42b opposite to the shank 41 for engagement with a screw driver. Other longitudinal bone anchors like pins, barbed or roughened nails can also be used.

Figure 2:
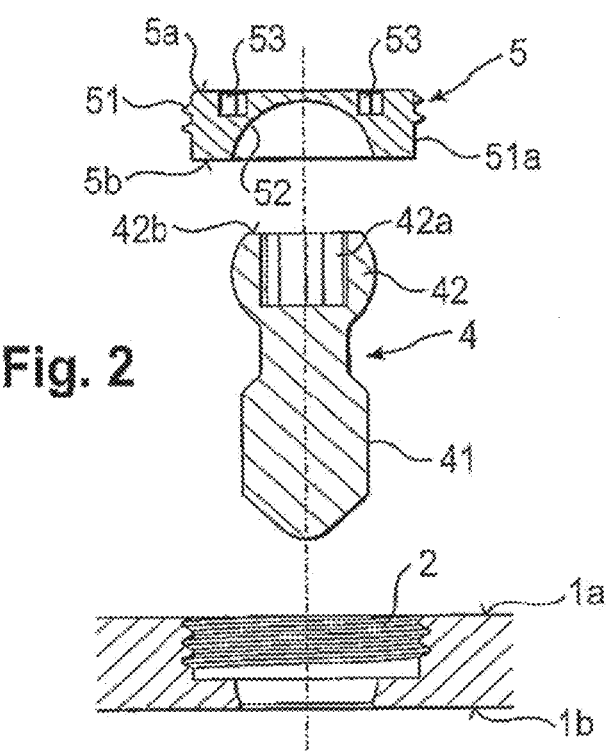
FIG. 2 shows a schematic exploded sectional view of the portion of the bone plate of FIG. 1 including a hole, a bone screw and a locking element.

As can be seen in FIGS. 1 and 2 a locking element 5 is provided for locking the bone screw 4 in the first holes 2 as described below.

Figure 3:
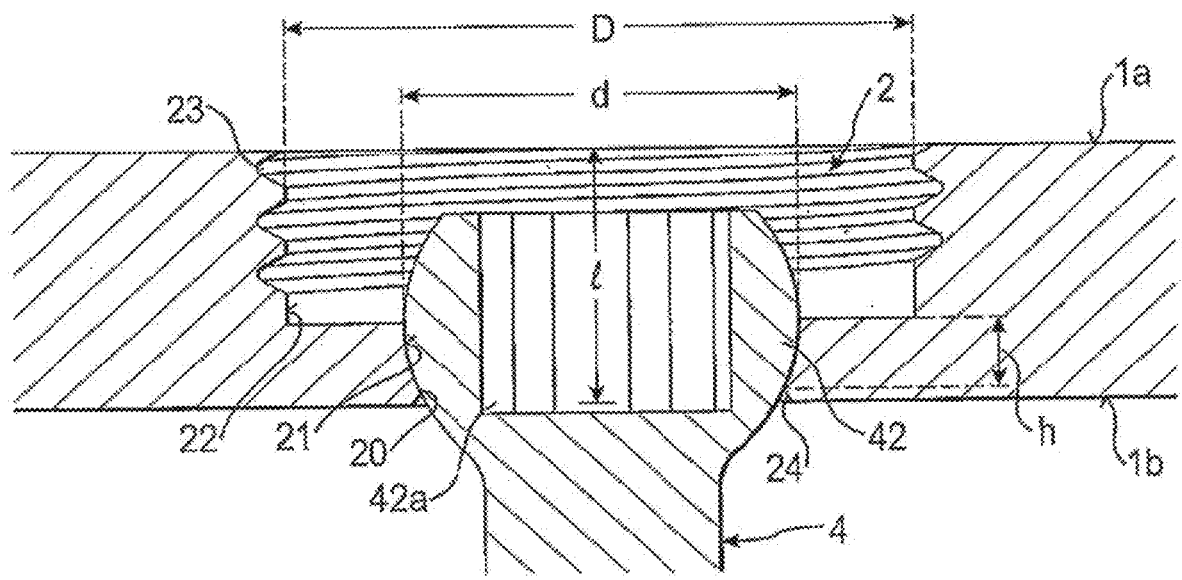
FIG. 3 shows a schematic sectional view of a portion of the bone plate of FIG. 1 including a hole and an inserted bone screw.

The structure of the first holes 2 will now be described with reference to a first hole 2 shown in FIGS. 3 and 4. The first hole 2 comprises an opening 20 at the bottom side 1b the inner diameter of which is larger than the outer diameter of the threaded shank 41 of the bone screw so that the threaded shank 41 can pass therethrough. The diameter is, however, smaller than the largest outer diameter d of the head 42 so that the head 42 cannot pass therethrough. Adjacent the opening 20 a hollow seat portion 21 is provided which forms a socket for a pivoting movement of the head 42. This allows insertion of the bone screw at any desired angle. In the embodiment shown, the seat portion 21 is spherically-shaped with a radius that matches the radius of the spherically-shaped portion of the head 42. When the head rests in the seat portion, a part of the spherical section of the head projects out of the bottom side 1b. The height h of the seat portion 21 is smaller than the radius of the head 42 and preferably smaller than half of, more preferably smaller than or equal to a quarter of the radius of the head 42. Between the seat portion 21 and the top side 1a a cylindrical bore 22 with a portion 23 having an internal thread is provided. As shown in FIG. 3, in one exemplary aspect of the invention, this internal thread is a full thread, reaching to the top of the cylindrical bore 22. The inner diameter of the bore 22 is larger than the inner diameter of the seat portion 21 and larger than the outer diameter of the spherical portion of the head 42. In other words, the inner diameter D of the bore 22 is larger than the outer diameter d of the head 42. By means of this, access to the head 42 with a screw driver is possible even at large pivot angles. For example, the inner diameter D of the bore 22 may, in one exemplary aspect of the invention, be approximately 1.2 to 1.7 times larger than the maximum outer diameter d of the head 42. However, this exemplary aspect is for illustration only and is not a limitation on the scope of the invention. The threaded portion 23 can have any thread form, for example a metric thread. The thickness 1 of the plate member 1 at the hole, that means the distance of the top side 1a from the bottom side 1b is smaller or equal to the largest outer diameter d of the head 42.

The opening 20 widens in a conical portion 24 towards the bottom side 1b to allow even larger pivot angles of the bone screw 4.

The locking element will now be described with reference to FIGS. 1, 2 and 4 to 7. The locking element is substantially cylindrical and has a top side 5a and a bottom side 5b and a threaded exterior surface portion 51 which cooperates with the internally threaded portion 23 of the bore 22 of the plate member. The height of the locking element corresponds substantially to the depth of the bore 22 so that when the locking element 5 is screwed into the bore 22 its top side 5a is substantially flush with the top side 1a of the plate member.

Figure 4:
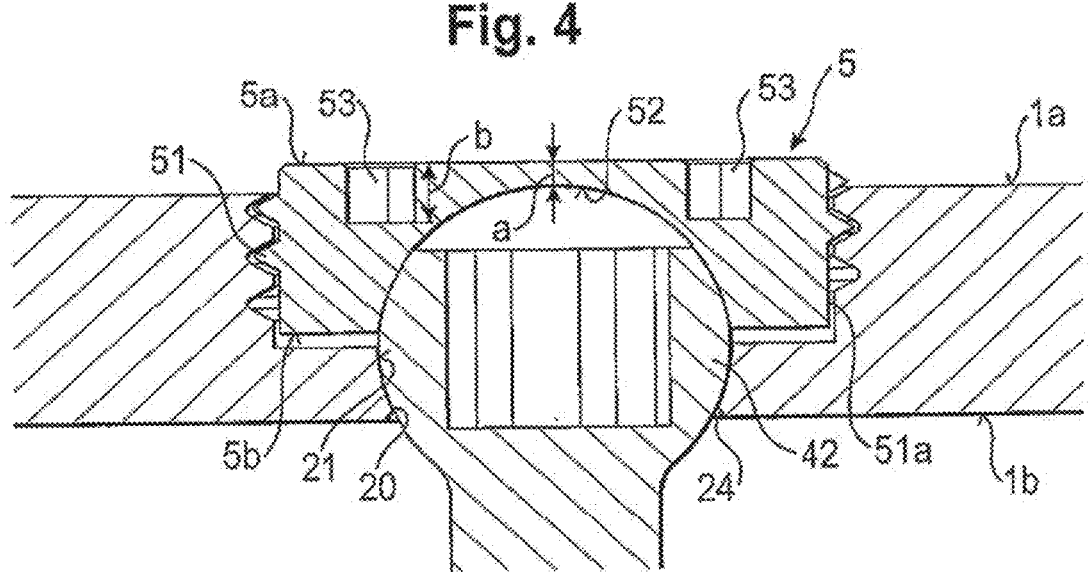
FIG. 4 shows a schematic sectional view of a portion of the bone plate of FIG. 1 with an inserted bone screw and a locking element.
Figure 5:
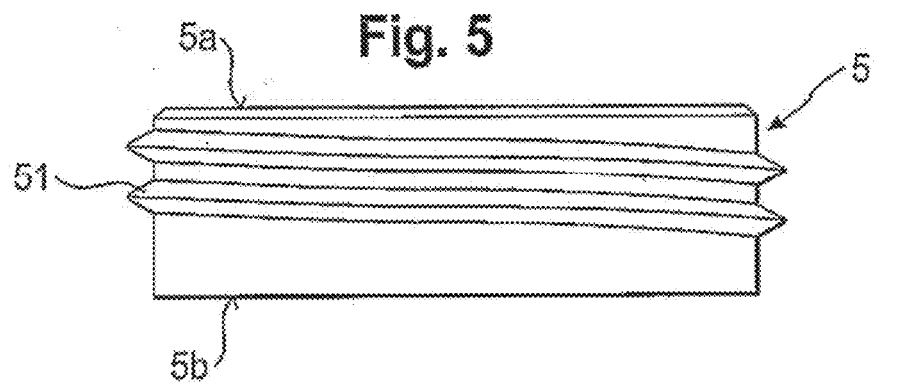
FIG. 5 shows a side view of the locking element of FIG. 4.

As can be seen in particular in FIG. 4, the locking element is partially threaded. The non-threaded portion 51a has an axial length which may be about equal to or smaller than that of the threaded portion 51. The locking element can also be fully threaded.

On the bottom side 5b the locking element 5 comprises preferably a spherically-shaped recess 52 which fits to the spherically-shaped portion of the head 42. The depth of the recess 52 can be equal to or larger than the radius of the spherical portion of the head 42. By means of this, the pressure exerted by the locking element 5 onto the head 42 is smoothly distributed onto the head 42.

Figure 6:
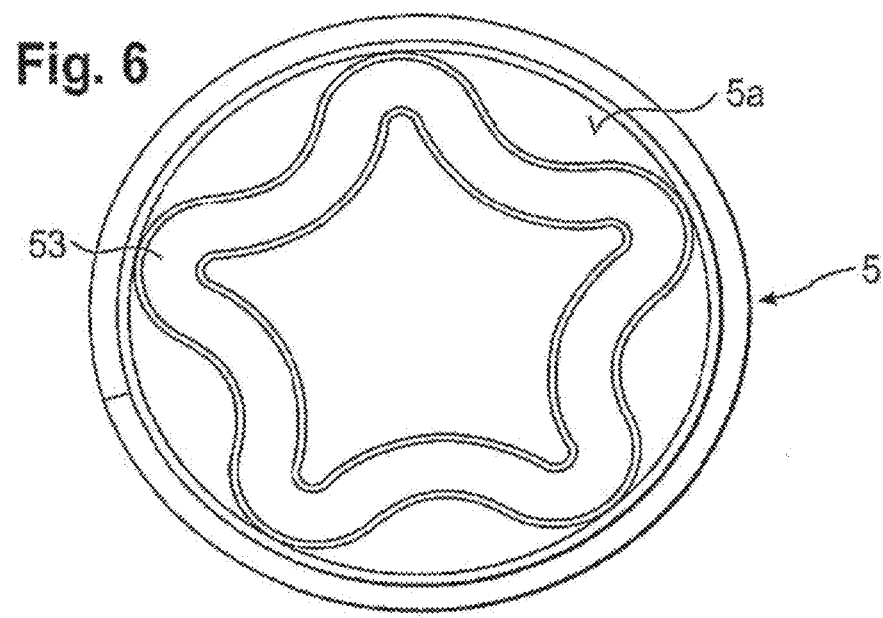
FIG. 6 shows a top view of the locking element of FIG. 4.
Figure 7:
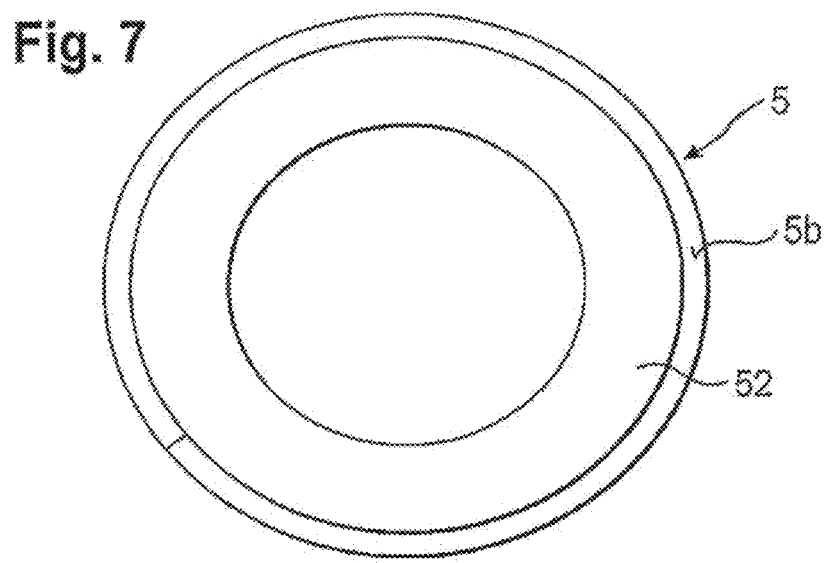
FIG. 7 shows a bottom view of the locking element of FIG. 4.

A recess 53 in form of a ring-shaped groove with a contour which allows a form-fit engagement of a corresponding tool which is provided in the outer radial area is provided in the top side 5a of the locking element 5. As shown in FIG. 6, the contour of the groove in this embodiment has a star-like shape. The central area of the top side 5a is solid, i.e. is without a recess.

As can be seen in particular in FIG. 4, the depth of b of the recess 53 is larger than the distance a of the deepest portion of the recess 52 from the top side 5a. Since the recess 53, which serves for engagement with a driver, is in the outer area of the top side 5a, the spherical recess 53 extending from the bottom side 5b can have a large depth which results in an increased contact area between the locking element 5 and the head 42. On the other hand, the seat portion 21 can be kept small to allow large angulation of the bone screw 4.

Furthermore, with the design described above the locking element has a reduced height. As a consequence thereof, the overall height of the bone plate assembly can be kept small.

It is possible to provide different locking elements which differ in their axial length or a different depth in the spherically-shaped recess to achieve either full locking of the head or a frictional locking. Frictional locking allows pivoting under application of an additional force which exceeds the frictional force between head and plate member. A further different locking element may have a length or a different depth in the spherically-shaped recess which allows a free pivotal movement of the screw with the locking element only preventing pull-out of the screw.

The overall height of the bone plate assembly can be further downsized by using a two-start thread for the threaded portions.

The design of the holes 2 and the locking element 5 are not restricted to the specific embodiment shown. For example, the seat portion 21 needs not to be spherically-shaped, but can have another shape such as a taper or even can be realized only by the edge of the opening 20. Between the seat portion 21 and the bore 22 transitional sections of the hole can be arranged provided they do not restrict the pivoting motion of the screw head. The bore 22 is shown to be cylindrically-shaped. However, it could also be a conical bore. The locking element would then be adapted thereto. Since only a relatively small clamping force is necessary to lock the angular position of the bone screw, other kinds of connections between the locking element and the bore can be used, for example, a bayonet locking structure. Also, the orientation of the holes in vertical direction needs not to be perpendicular to the surface but can include an angle with the normal onto the surface of the plate member for providing an initial angulation.

Figure 8:
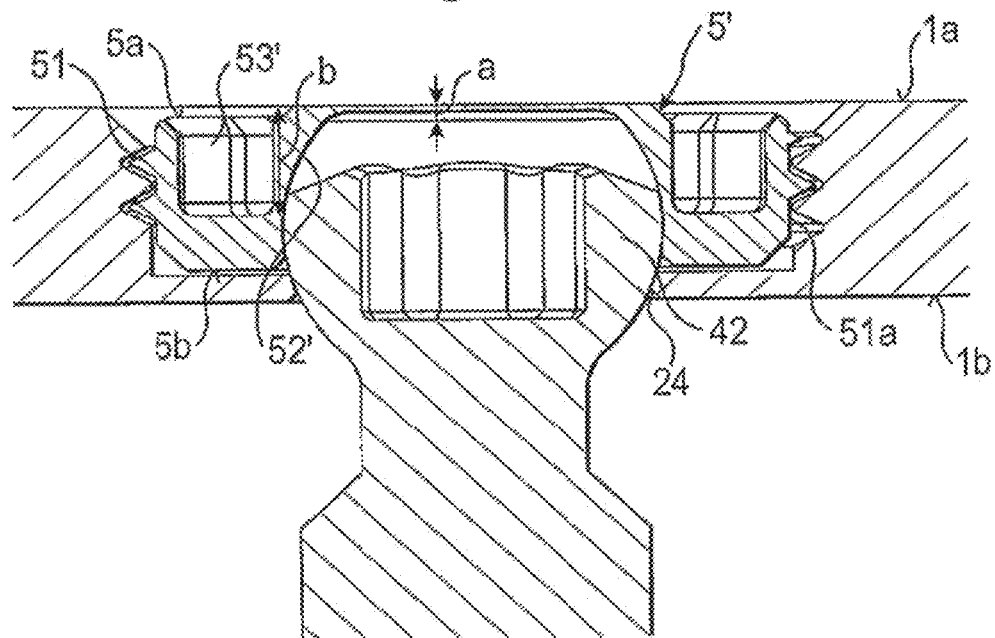
FIG. 8 shows a schematic sectional view of a portion of the bone plate of FIG. 1 with an inserted bone screw in a vertical position and a slightly modified locking element.
Figure 9:
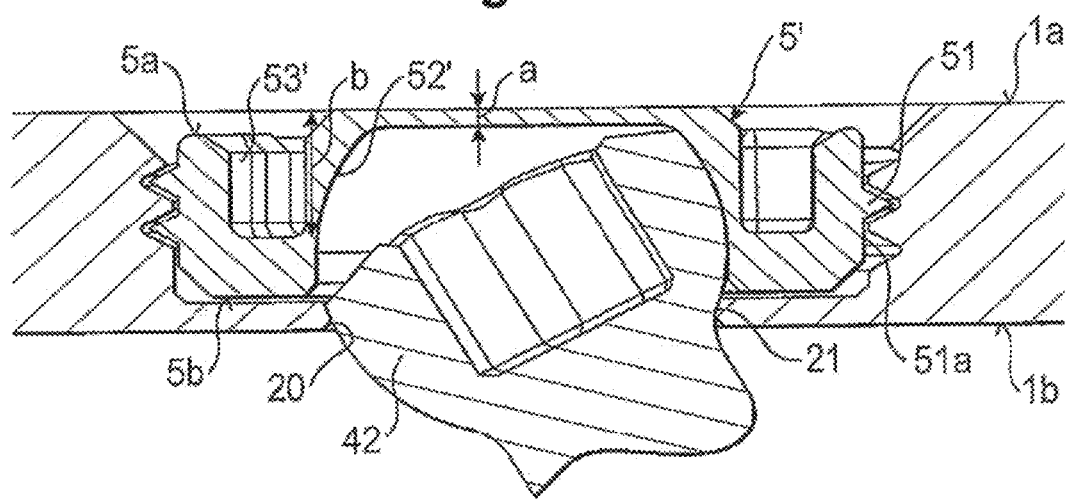
FIG. 9 shows the arrangement of FIG. 8 with the bone screw in a pivoted position.

In FIGS. 8 and 9, the locking element 5 is slightly modified in such a way that the recess 53 is closer to the outer edge than in the locking element 5 shown in FIG. 4. The recess 52' is deeper than the recess 52 of the locking element of FIG. 4 and has a flat portion near the top side 5a. The profile of the assembly can be further downsized by this design.

The recess 53 forms a drive portion for a tool such as a screw driver. It is not restricted to the shown star-like contour but can also have other shapes such as, for example, a polygon, a wavy or a flower-like contour or can have interruptions so that only groove portions or recesses are provided.

With the design described above a large pivot angle such that a range of motion of at least 60° up to 70° can be achieved.

Figure 10:
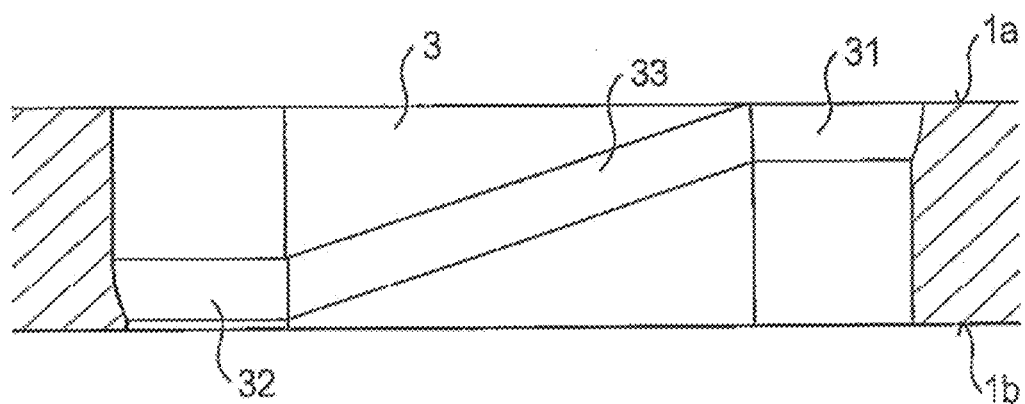
FIG. 10 shows a schematic sectional view of a portion of the bone plate of FIG. 1 including a second type of hole.
Figure 11:
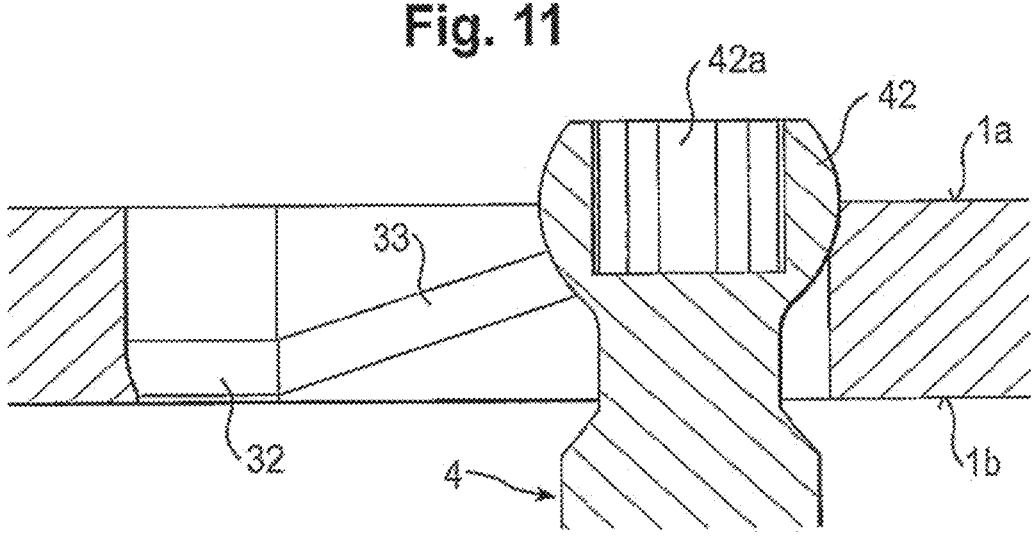
FIG. 11 shows a schematic sectional view of a portion of the bone plate of FIG. 1 including the second type of hole with an inserted bone screw.

Next, the second holes 3 are described with reference to FIGS. 1, 10 and 11. The second holes 3 have a substantially oblong shape with the long side oriented in the direction of the longitudinal axis L. As can be seen in particular in FIG. 10, a hole 3 has an upper seat portion 31 which has the shape of a hollow spherical section matching the exterior spherical surface portion of the head 42. Further, a lower seat portion 32 is provided at the opposite short side of the oblong hole 3 adjacent the bottom side 1b. The shape of the seat portion 32 is also spherical and matches the shape of the exterior surface portion of the head 42. Between the upper seat portion 31 and the lower seat portion 32 an inclined spherical groove 33 extends along the inner wall of the long side of the oblong hole, the size of which is adapted to the exterior surface portion of the head 42 so that the head 42 can be guided along the groove 33.

The elements of the bone plate assembly are made of a body compatible material, such as a body compatible metal, for example stainless steel or titanium or a body compatible metal alloy such as Ni—Ti alloys, for example Nitinol, or of a body compatible plastic material, for example medical grade PEEK or of combinations thereof. For example, the plate member, the locking elements and the bone anchors can be made of different materials.

Now, use of the bone plate assembly according to the first embodiment will be described. First, the number of bone screws necessary for the stabilization of the bone parts or bone fragments is determined. It should be noted that in some cases it is not necessary to use all the holes provided on the plate member. Holes which are not used for bone screws may be closed by a plug member to be described below. Once, the necessary number and types of the screws are determined, the screws are inserted into the first holes 2 and/or second holes 3. After positioning the plate member at the fracture site the screws are inserted into the bone parts at the desired angle. The bone screws are inserted into the holes at this desired angle and the spherical seat allows placement of the head of the screw in the hole at this angle. After full insertion of bone screws the head 42 of each bone screw, which is inserted into a first hole 2, abuts against the seat portion 21 of the hole 2. Already in this condition the angle between the bone screw and the plate member is fixed when at least two bone screws are inserted. To further stabilize the connection between the bone screw and the plate the locking element 5 can be used which is inserted into the bore and tightened so that it locks the head in the selected angular position. If desired, different locking elements can be applied to different screws in order to provide for full locking, frictional locking or free angulation with the locking member only preventing pull-out of the screw as described above.

The holes 3 are used for providing a self-compression effect. The bone screws 4 which are inserted into the oblong holes 3 are oriented substantially vertically relative to the plate member. The screw head 42 which is first seated in the upper seat portion 31 slides downwards along the inclined groove 33 until it rests in the lower seat portion 32. Preferably, the second holes are arranged such that the lower seat portion 32 faces the center of the plate member. Since the screw head 42 is fixedly connected to the threaded shank 41 which is screwed into the bone the movement of the head 42 along the groove 33 leads to a movement of the bone part or fragment relative the plate and as a result to a compression of the bone parts against each other and against the plate member.

A second embodiment will be described with reference to FIGS. 12 to 14. Parts which are the same as those of the previous embodiments are designated with the same reference numerals and the description thereof is not repeated. As can be seen in FIG. 12 the plate member 1' has a contoured shape. The outer contour in a top view is slightly trapezoidal with rounded corners and a broadened middle portion. Further, spherically shaped recesses 7 are provided at the lower side 1b to reduce the contact area with the bone. A minimal contact area of the plate member with the bone surface may be required in certain cases to prevent injury of the bone surface and compression of blood vessels etc.

The recesses 7 also result in plate member portions with different thickness. The plate can be bent in portions with a smaller thickness the bone plate assembly can be used as a dynamic compression plate.

In this embodiment, two holes are provided at the short sides 1c and three holes are provided in the center of the plate in a longitudinal axis. The holes 2 may be offset from the longitudinal axis. The number is not limited to the number shown but can vary. Between the holes 2 near the short sides 1c and the holes 2 in the center second holes 3 may be provided for self-compression.

In the case of small bone fragments which shall be immobilized by means of the bone plate assembly not all holes may be used for bone screws 4. As shown in FIGS. 12 and 13, for example, the first holes 2 in the center section of the plate member are not used for screws. They may be closed by a plug member 8 shown in FIG. 14. The plug member 8 is substantially cylindrical with a top side 8a and a bottom side 8b. It has a first portion 81 which has a threaded portion 82 cooperating with the threaded portion 23 of the bore 22. The first portion 81 fits into the bore 22 so that the top surface 8a is substantially flush with the top surface 1a of the plate member 12'. A recess 53 which has an approximate star-shape is provided in the top surface 8a of the plug member as for the locking element 5. The plug member can prevent cracking or breaking of a plate member at the thinned portions 7.

Adjacent the cylindrical portion 81 the plug member 8 has a spherically shaped projection 83 which fits into the seat portion 21 of the hole 2 so that after insertion of the plug member 8 the hole 2 is closed. The bottom side 8d may be flush with the bottom side 1b of the plate member.

Alternatively, a locking element as described above can be used as a plug member.

In a further embodiment, the bone plate assembly includes a modified locking element as shown in FIGS. 15a), 15b). The locking element 5' differs from the locking element of the previous embodiments by the shape of the recess 53''' at the top side 5a of the locking element which serves for the driver. Further a coaxial through-hole 54 is provided. All other features of the locking element are the same or can be present in the same manner as for the locking element of the previous embodiments. The coaxial through-hole 54 extends from the top side 5a through the locking element and continuous in the recess 52. The diameter of the coaxial through-hole is configured. Hence, the diameter of the through-hole can be larger than the diameter of the free end 42b of the screw head 42. This enables the screw head 42 to at least partly extend into the through-hole 54. The coaxial through hole 54 allows to further reduce the thickness of the plate member and the locking element, since the head of the screw can partially extend into the hole when the screw is in an angled position as shown in FIG. 15b)

The recess for the driver which is used to tighten the locking element 5' is in this embodiment composed of a plurality of spaced apart recesses forming elongate pockets 53''' which are arranged around the central axis of the locking element in a circumferential manner.

The depth of the pockets 53''' is configured such that the pockets extend below the free end 42b of the screw head when the screw head 42 rests in the seat 21. In other words, the distance b of the deepest portion of the pockets 53'' from the top side 1a is larger than the deepest portion of the recess 52 from the top side 1a in the previous embodiments. Since the recess 53'' extends into the body of the locking element in an area around the screw head the locking element has a small thickness. Therefore, a low profile polyaxial locking plate is provided. In a modified embodiment the recess may extend completely through the locking element.

In a further modification shown in FIG. 16, the locking element 5'' has an annular rim 55 on the top side 5a.

Figure 17A:
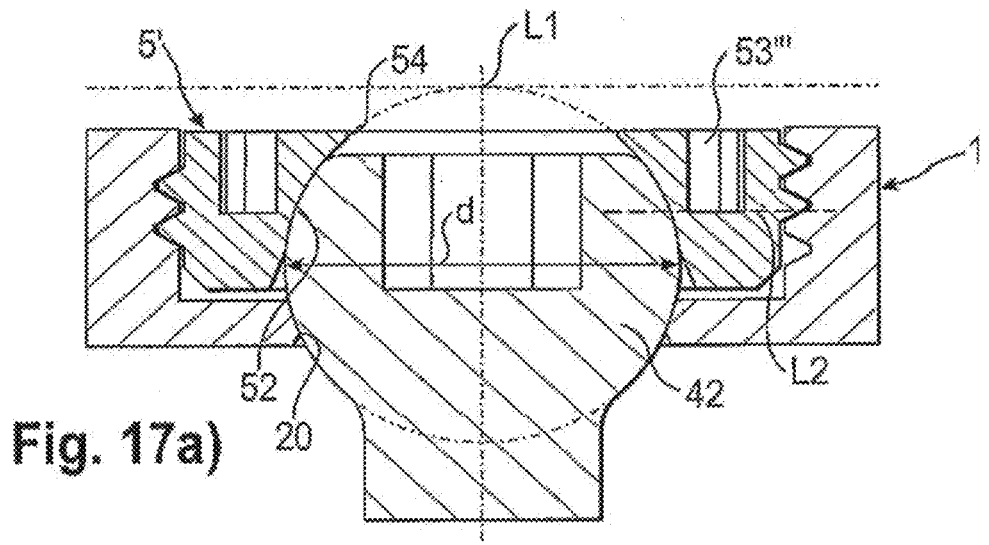
FIGS. 17a) to 17e) show a schematic sectional view of a portion of the bone plate with a polyaxial bone screw and a locking element, respectively, to illustrate a dimensional relationship between the recess for the driver and the head of the bone screw.

In FIGS. 17a) to 17e) schematic sectional views of a portion of the bone plate assembly with a polyaxial bone screw and a locking element are shown that explain a dimensional relationship of the recess for the driver and the head of the bone screw. In FIG. 17a) a locking element is shown wherein the recess 52 for the head extends into the top side 5a so that a through-hole 54 is formed. A first level L1 is defined by the highest point of a circle that is drawn around the screw head with a diameter that corresponds to the largest diameter d of the screw head. The largest diameter d of the screw head 42 is located above the opening 20 on the bottom side of the bone plate. The bottom of the recess 53''' for the driver defines a second level L2. As shown in FIG. 17a), the level L2 is below L1. With this relationship the bone plate assembly has a low profile. Simultaneously, a large range of angulation of the screw can be achieved.

Figure 17B:
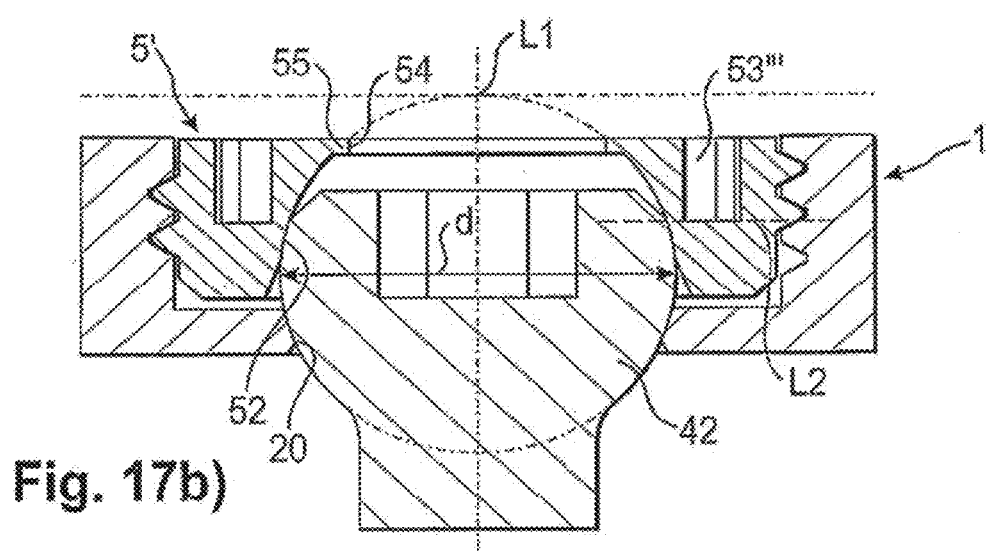

In FIG. 17b) the locking element is similar to the locking element shown in FIG. 16 and has an annular rim 55 at the top side. Also in this case, the highest point of a circle which is projected from the position of the greatest diameter d of the screw head defines a level L1 and the bottom of the recess 53''' defines a level L2 which is below L1.

Figure 17C:
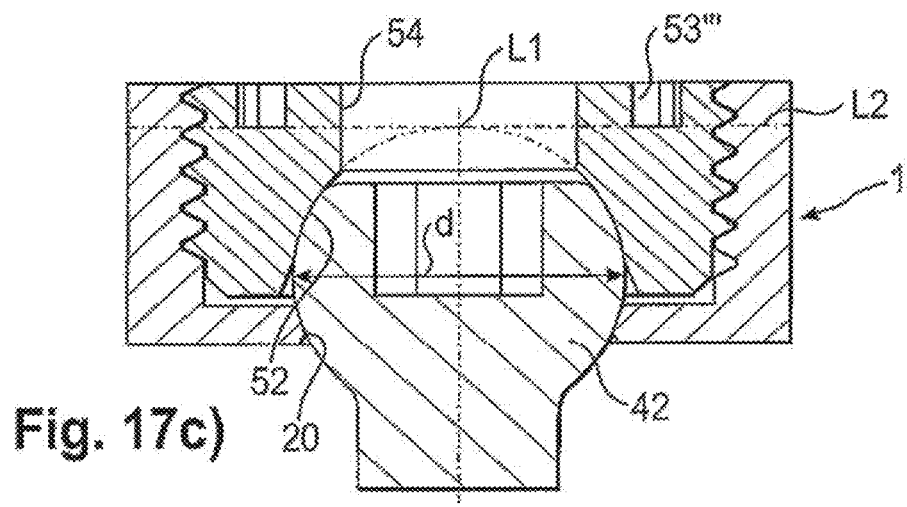

FIG. 17c) shows a locking element that has the highest point of a circle projected from the position with the largest diameter d of the screw head 42 on a level L1 which is on the same level L2 as the bottom of the recess 53''' for the driver. A low profile can still be obtained.

In FIG. 17d) the top surface 5a of the locking element is closed. The highest point of the circle is above the closed top surface. Also in this case the level L2 is below L1.

FIG. 17e) shows a locking element which has a conically-shaped first recess 52' which contacts the head 42 of the polyaxial bone screw 4. Also in this case the level L2 is the same as the level L1 or below L1.

The contact area between the screw head 42 and the recess 52 is not limited to a spherical surface, it can be a line contact or can have another shape. Thus, the recess 52 for the screw head is not limited to a spherical or a conical form but can have various shapes.

The screw head needs not to be completely spherical. It is sufficient that it has a spherically shaped surface portion. It can also be shaped otherwise, as long as it can pivot in the seat.

FIGS. 18 to 20 show a tool for use with locking element and the bone plate assembly. The tool 60 comprises a driver 61 with an engagement portion 62 for engaging the locking element and a handle 63. The engagement portion 62 of the driver 61 is configured to engage the engagement structure such as the pockets 53''' in the locking element 5' of FIGS. 15 and 16 or the groove 53 in the locking element 5 of FIGS. 1 to 9. The driver 61 extends with its engagement portion 62 through a tubular holder 64 and is axially movable and rotatable therein. The holder 64 has at a distance from its free end which faces away from the handle 63 a radial slot 65 which is configured to pass the locking element 5 therethrough. Further, the counter holder 64 has at its free end a portion with an internal thread 66 cooperating with the external thread 51 of the locking element 5.

Figure 21A:
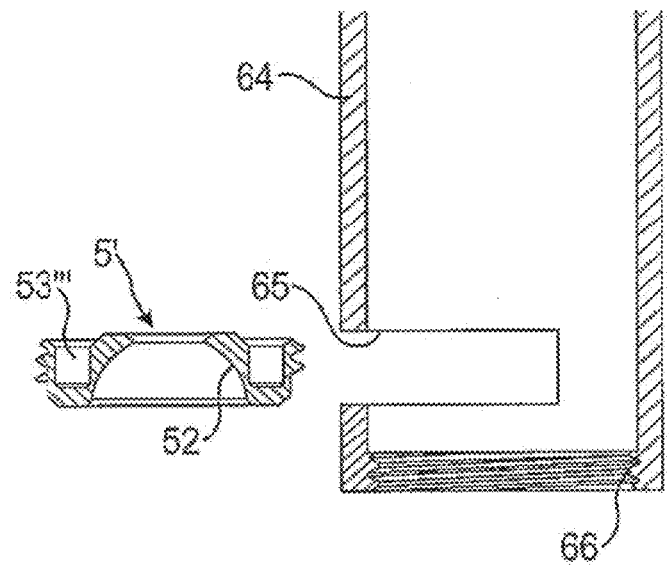
FIGS. 21a) to 21d) show steps of using the tool.
Figure 21B:
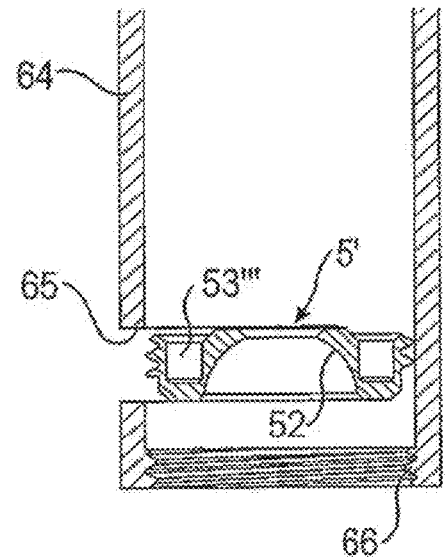
Figure 21C:
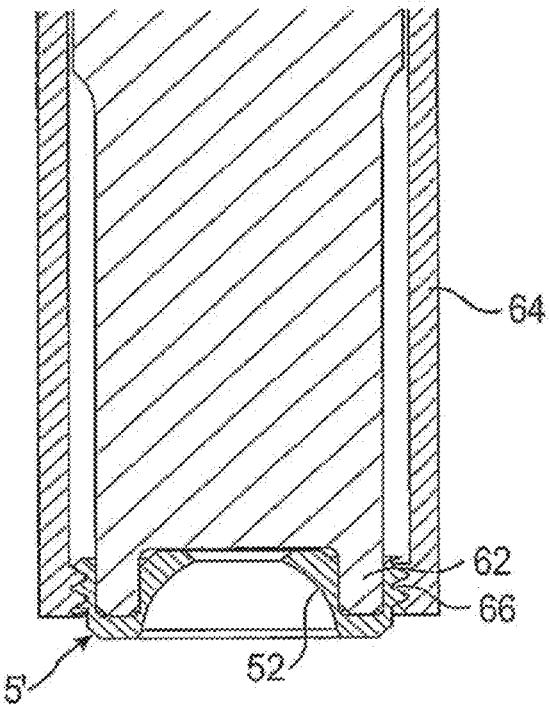
Figure 21D:
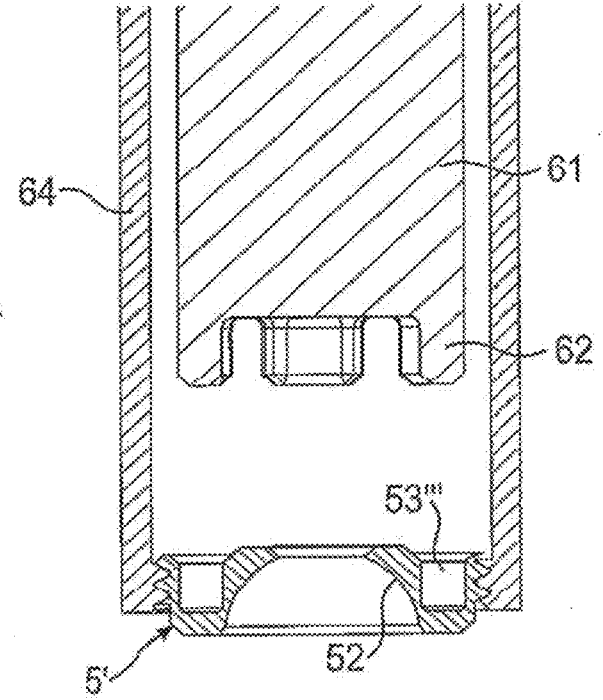

The steps of taking up the locking element with the tool 60 are schematically shown in FIGS. 21*a*) to 21*d*). Exemplary the locking element of FIGS. 15 and 16 is shown. In a first step, the driver 61 is retracted and the holder 64 is free at the location of the slot 65. In a next step as shown in FIG. 21*b*) the locking element 5' is introduced through the slot 65 into the holder 64. The bottom side 5*b* of the locking element, which has the recess 52 for the head, faces the threaded portion 66 of the holder 64. Then, as shown in FIG. 21*c*), the driver 61 is moved through the holder 64 to engage the pockets 53''' and the locking element 5' is screwed into the threaded portion 66 of the holder 64. Then, as shown in FIG. 21*d*), the driver 61 can be retracted and the locking element can be placed into the hole 2. Finally, as shown in FIG. 20 before, the driver 61 can be advanced again and engage the pockets 53''' of the locking element to screw the locking element further into the hole 2. If desired, the locking element is tightened to press onto the head to fix the angular position of the bone screw.

With the tool, the locking element can be safely taken up and held in the holder. In addition, it can be safely placed into the hole and inserted therein.

Referring again to the locking element, it may be configured to be used with a polyaxial bone anchor, and be substantially cylindrical with a bottom side (5*b*) facing a head (42) of the bone anchor, a top side (5*a*) opposite to the bottom side (5*b*), and a surface portion with an external thread. The locking element may have a first recess (52, 52') at the bottom side for accommodating at least a portion of the head (42), and a second recess (53, 53', 53''') at the top side (5*a*) for engagement with a driver, the second recess being located outside the center of the top side (5*a*). The head (42) may have a portion with a largest diameter (d), and a first level L1 defined by the highest point of a circle with the largest diameter drawn around the head, and a second level L2 is defined by the bottom of the second recess (53, 53', 53'''), L2 being at a level not higher than L1.

The locking element may include a coaxial through-hole (54). A contact area of the first recess (52) that contacts the head may be a conically shaped contact, a line contact, and/or a spherically-shaped contact. The second recess (53, 53'', 53'') may be located substantially in a radially outer area of the top side (5*a*). The second recess (53, 53') may include a ring-shaped groove with a contour configured have formfitting engagement with the driver. The contour may be selected from at least one of the group consisting of a star-like contour, a polygonal contour, and a flower-like contour. The second recess may include a plurality of pockets (53'''). The pockets may be configured to extend through the locking element into the bottom side (5*b*). A distance (a) of a deepest portion of the second recess (52), measured from the top side (5*a*) is smaller than a depth (b) of the first recess (53, 53', 53'') measured from the top side (1*a*). The locking element may also include a portion (51) with an external thread. The locking element (5) may include a portion with the external thread that spans the entire locking element (5), making the locking element (5) fully threaded, and/or a portion with the external thread that does not span the entire locking element (5), having a non-threaded section (51*a*) adjacent the bottom side (5*b*). An axial length of the non-threaded section (51*a*) may be substantially equal to or smaller than the axial length of a threaded section of the portion with the external thread (51).

Referring again to a bone plate assembly, it may include an elongate plate member (1, 1') with a top side (1*a*) and a bottom side (1*b*), at least two holes (2, 2, 3) extending from the top side to the bottom side, and at least two bone anchors (4), each bone anchor comprising a shank (41) configured to anchor into the bone, and a head (42) having a portion with a largest outer diameter (d), wherein the shank is extendable through the hole. At least one of the holes (2) may be configured to define a seat (21) at the bottom side (1*b*) adapted to pivotably receive the head (42), wherein the at least one of the holes (2) includes a bore (22) at the top side (1*a*) with a bore axis and an inner diameter (D) at least as large as the largest diameter (d) of the head (42). The locking element (5, 5', 5'', 5''') may be configured to be inserted into the bore (22), having a central axis coaxial with the bore axis, a bottom side (5*b*) facing the head, and a top side (5*a*) facing away from the head. The locking element may have a first recess (52, 52') at the bottom side for at least partially covering the head, and a second recess (53, 53', 53''') at the top side (5*a*) for engagement with a driver, the second recess being located outside the center of the top side (5*a*). The highest point of a circle with the largest diameter (d) that is drawn around the head may define a first level L1 and the bottom of the second recess (53, 53', 53''') may define a second level L2, which is at a level not higher than L1.

The bone plate assembly may include a plurality of locking elements and these may be configured to lock the head and/or prevent loosening of the bone anchoring element and/or bone plate assembly, while allowing pivotal movement.

Referring once again to a bone plate assembly, it may include an elongate plate member (1, 1') with a top side (1*a*) and a bottom side (1*b*), at least two holes (2, 2, 3) extending from the top side to the bottom side, and at least two bone anchors (4), each bone anchor comprising a shank (41) configured to anchor into the bone, and a head (42) having a top (42*a*) and a portion with a largest outer diameter (d), wherein the shank is extendable through the hole. At least one of the holes (2) may be configured to define a seat (21) at the bottom side (1*b*) adapted to pivotably receive the head, (42) wherein the at least one of the holes includes a bore (22) at the top side (1*a*) with a bore axis and an inner diameter (D) which is at least as large as the largest diameter (d) of the head (42). It shall be understood by one of ordinary skill in the art, that the head may be pivotably received when a bone anchor is inserted into the bone plate assembly, for example. However, at such times as, for example, upon insertion of the bone anchor into bone, pivoting may be restricted. A locking element (5, 5') is configured to be inserted into the bore and having a central axis coaxial with the bore axis, a bottom side (5*b*) facing the head, a top side (5*a*) facing away from the head and a recess (53, 53', 53'') at the top side (5*a*) configured to be engaged with a driver, the recess being located outside the center of the top side (5*a*) and having a depth that extends below the top (42*a*) of the screw head (42) when the screw head (42) is in the seat (21).

The bore may have a portion (23) with an internal thread and the locking element (5) may have a portion (51) with an external thread adapted to cooperate with the internal thread of the bore. At least one of the internal thread and the external thread may include a two-start thread. Furthermore, another locking element may be included in the bone plate assembly, and the locking element and the another locking element may have different axial lengths. The first recess (52) may include a spherical shape and a depth measured from the bottom side (5*b*) substantially equal to or slightly larger than half of the diameter (d) of the head. The bone plate assembly may also include a plug member (8) adapted to close a hole if a bone anchor is not used.

Referring now to a tool adapted for use with a bone plate assembly described herein, it may include a driver (61) with an engagement portion (62) configured to engage a locking element; and a tubular holder (64). The driver may be configured to extend with the engagement portion (62) through the tubular holder (64), and may be axially movable and rotatable within the holder. The holder may have a radial slot (65) adapted for insertion of the locking element. The holder may include a portion with an internal thread (66) for cooperation with an external thread (51) of the locking element.

The shape of the plate member is not restricted to the embodiments shown. Other shapes are also conceivable. The bone anchor is not limited to a bone screw which has a threaded shank. Smooth, barbed or roughened pins are also conceivable. Further, any known bone screws may be used. Additionally, other bone anchors may be used.

What is claimed is:

1. A tool for use with a locking element having a recess and external threads, comprising:
    an elongate driver having a proximal end and a distal end, and a longitudinal central axis extending from the proximal end to the distal end, the distal end having an engagement portion configured to engage the recess of the locking element; and
        an elongate tubular holder having a proximal end and a distal end, the distal end of the holder having an interior with an internal thread and a distal opening, the interior defining a diameter, and the holder having a radial slot proximal of the internal thread adapted through which to side load the locking element into the holder, the radial slot has a height parallel with a longitudinal axis of the holder, and the diameter of the holder is greater than the height of the radial slot,
    the driver adapted to extend within the holder from the proximal end of the holder to the distal end of the holder, wherein the driver is axially movable and rotatable within the holder to engage and rotationally advance the locking element through the distal end of the holder in contact with the internal threads and then out of the distal opening at the distal end of the holder.

2. The tool of claim 1, wherein:
the driver includes a handle at its proximal end.

3. The tool of claim 1, wherein:
the driver is longer than the holder.

4. The tool of claim 1, wherein:
at least a portion of the driver is close fitting with the holder.

5. The tool of claim 1, wherein:
the engagement portion is not located on the longitudinal central axis of the driver.

6. The tool of claim 5, wherein:
the engagement portion is one of ring-shaped, star-shaped, and wavy.

7. A locking system for use with a bone plate having a screw hole with a threaded upper portion and a screw seat in which a polyaxial bone anchor having a head is received, the locking system comprising:
    a) a locking element including a central axis, a bottom side, a top side opposite to the bottom side, and a peripheral surface portion that extends completely around the locking element that has an external thread, wherein
        the bottom side defines a first recess facing toward the bottom side for accommodating and applying a force in a direction toward the bottom side to the head of the polyaxial bone anchor, and
        the top side defines a second recess off the central axis and having a non-circular cross-section in a plane perpendicular to the central axis;
    b) a tool, including
        an elongate driver having a proximal end and a distal end, the distal end having an engagement portion configured to engage the second recess of the locking element, and
        an elongate tubular holder having a proximal end and a distal end, the distal end of the holder having an interior with an internal thread and an opening, and the holder having a radial slot into the interior proximal of the internal thread through which the locking element is side loaded into the holder, the driver adapted to extend within the interior of the holder from the proximal end of the holder to the distal end of the holder, wherein the driver is axially movable and rotatable within the holder to engage the second recess of the side loaded locking element and rotationally advance the locking element through the distal end of the holder in contact with the internal threads and then out of the opening at the distal end of the holder.

8. The locking system of claim 7, wherein:
the driver includes a handle at its proximal end.

9. The locking system of claim 7, wherein:
at least a portion of the driver is close fitting with the holder.

10. The locking system of claim 7, wherein,
the locking element has a diameter and a height between the top side and the bottom side extending in a direction parallel to the central axis of the locking element, and the diameter of the locking element is greater than the height of the locking element, and
the interior of the holder has a diameter, and the radial slot has a height extending in the same direction as the height of the locking element when the locking element is side loaded therethrough, and the diameter of the interior of the holder is greater than the height of the radial slot.

11. A locking system for use with a bone plate having a screw hole with a threaded upper portion and a screw seat in which a polyaxial bone anchor having a head is received, the locking system comprising:
    a) a locking element including a central axis, a bottom side, a top side opposite to the bottom side, and a peripheral surface portion that extends completely around the locking element that has an external thread, wherein
        the bottom side defines a first recess facing toward the bottom side for accommodating and applying a force in a direction toward the bottom side to the head of the polyaxial bone anchor, and
        the top side defines a second recess;

b) a tool, including
- an elongate driver having a proximal end and a distal end, the distal end having an engagement portion configured to engage the second recess of the locking element, and
- an elongate tubular holder having a proximal end and a distal end, the distal end of the holder having an internal thread that threadedly engages the external thread of the locking element, and the holder having a radial slot proximal of the internal thread through which the locking element is received,
- the driver adapted to extend within the holder from the proximal end of the holder to the distal end of the holder, wherein the driver is adapted to engage the second recess of the locking element inserted through the radial slot and the driver is axially movable and rotatable within the holder to apply torque to the locking element.

12. The locking system of claim 11, wherein:
at least a portion of the driver is close fitting with the holder.

13. The locking system of claim 11, wherein,
the holder has an interior with a diameter, and the radial slot has a height parallel with a longitudinal axis of the holder, and the diameter of the holder is greater than the height of the radial slot.

* * * * *